United States Patent [19]

Lee et al.

[11] Patent Number: 5,004,841

[45] Date of Patent: * Apr. 2, 1991

[54] ALKYLATION OF AROMATIC COMPOUNDS TO ALKYLATES ENRICHED IN THE LINEAR-SUBSTITUTED ISOMERS

[75] Inventors: Guo-shuh J. Lee; Juan M. Garces; Joseph J. Maj, all of Midland; Stephen C. Rocke, Mt. Pleasant, all of Mich.

[73] Assignee: The Dow Chemical Company, Midland, Mich.

[*] Notice: The portion of the term of this patent subsequent to Jan. 2, 2007 has been disclaimed.

[21] Appl. No.: 323,530

[22] Filed: Mar. 14, 1989

Related U.S. Application Data

[63] Continuation-in-part of Ser. No. 123,741, Nov. 23, 1987, Pat. No. 4,891,448.

[51] Int. Cl.$^5$ .............................................. C07C 41/00
[52] U.S. Cl. ........................................ 568/678; 568/27; 568/29; 568/33; 568/34; 568/36; 568/37; 568/53; 568/57; 568/58; 568/68; 568/707; 585/452; 585/453
[58] Field of Search ............. 568/628, 27, 29, 33, 568/34, 36, 37, 53, 57, 58, 68, 707; 585/452, 453

[56] References Cited

U.S. PATENT DOCUMENTS

| | | | |
|---|---|---|---|
| 3,251,897 | 5/1966 | Wise | 260/671 |
| 3,551,510 | 12/1970 | Pollitzer et al. | 260/672 |
| 3,597,493 | 8/1971 | Frilette et al. | 260/666 |
| 3,716,597 | 2/1973 | Mitsche et al. | 260/671 C |
| 3,849,340 | 11/1974 | Pollitzer | 252/455 Z |
| 4,085,156 | 4/1978 | Frilette et al. | 260/671 R |
| 4,283,573 | 8/1981 | Young | 568/794 |
| 4,301,317 | 11/1981 | Young | 585/455 |
| 4,323,481 | 4/1982 | Kaduk | 252/455 Z |
| 4,420,418 | 12/1983 | Chu | 502/77 |
| 4,731,497 | 3/1988 | Grey | 585/455 |
| 4,891,448 | 1/1990 | Garces et al. | 568/628 |

FOREIGN PATENT DOCUMENTS 56-133224 10/1981 Japan.
58-159427 9/1983 Japan.

OTHER PUBLICATIONS

Derwent 84-026354/05 (1984).
K. A. Becker, H. G. Karge, and W.-D. Streubel, Journal of Catalysis, 28, 403-413 (1973).

Primary Examiner—Bruce Gray

[57] ABSTRACT

Aromatic compounds, such as benzene or biphenyl, are alkylated with an alkylating agent having from one to eight carbons atoms, such as propylene, in the presence of an acidic mordenite zeolite catalyst under conditions sufficient to produce a mixture of substituted aromatic compounds enriched in the linear alkylated isomers, such as p-diisopropylbenzene or p,p'-di(isopropyl)-biphenyl, respectively. The novel acidic mordenite catalyst is characterized by its silica/alumina molar ratio, its porosity, and a Symmetry Index. The p,p'-disubstituted isomers of aromatic compounds are useful as monomers in the preparation of thermotropic, liquid crystal polymers.

28 Claims, No Drawings

ALKYLATION OF AROMATIC COMPOUNDS TO ALKYLATES ENRICHED IN THE LINEAR-SUBSTITUTED ISOMERS

CROSS REFERENCE TO RELATED APPLICATION

This is a continuation-in-part of application Ser. No. 123,741, filed Nov. 23, 1987, now U.S. Pat. No. 4,891,448.

BACKGROUND OF THE INVENTION

This invention relates to mordenite zeolites and their use as catalysts in the alkylation of aromatic compounds to alkylates enriched in the linear-substituted isomers, such as the para isomers.

The para,para'-dialkylates (p,p'-dialkylates) of aromatic hydrocarbons, such as 4,4'-dialkylated biphenyl or 2,6'-dialkylated naphthalene, are valuable intermediates in the preparation of monomers from which thermotropic liquid crystal polymers are synthesized. Liquid crystal polymers are high molecular weight polymers which naturally exist in or can form liquid-crystal states. The liquid-crystal state is a highly anisotropic fluid state which possesses some properties of a solid and some properties of a conventional, isotropic liquid. For example, the typical liquid crystal flows like a fluid, while retaining much of the solid state molecular order. Thermotropic liquid crystals refer to those liquid crystals which are formed by the adjustment of temperature. Generally, for a molecule to possess a liquid-crystal state the molecule must be elongated and narrow, and the forces of attraction between these molecules must be strong enough for an ordered, parallel arrangement to be maintained after melting of the solid. Thus, bulky substituents positioned anywhere but on the ends of an elongated molecule will usually destroy the liquid-crystal state. Accordingly, p,p'-disubstituted aromatic compounds are likely to exhibit liquid crystalline properties, whereas meta- and ortho-disubstituted aromatic compounds are not. Thermotropic, liquid crystal polymers find utility in the formation of ultra high-strength fibers and films. An overview of liquid crystals may be found in Kirk-Othmer *Encyclopedia of Chemical Technology*, 3rd ed., Volume 14, John Wiley & Sons, New York, N.Y., pp. 395–427.

One group of monomers from which thermotropic liquid-crystal polymers are synthesized is the p,p'-dihydroxy polynuclear aromatics. Phenol, for example, is dialkylated at the ortho positions with isobutylene, and the resulting dialkylated phenol is coupled at the para position to form 3,3'5,5'-tetra(t-butyl)-4,4'-dihydroxybiphenyl. (See U.S. Pat. No. 4,108,908.) This substituted biphenyl is dealkylated to yield p,p'-dihydroxybiphenyl, which reacts with aromatic diacids and hydroxy acids to form liquid crystal polymers. Aromatic diacids are also prepared in a multi-step process p-Chlorotoluene, for example, is coupled to form 4,4'-dimethylbiphenyl, which is subsequently oxidized to 4,4'-biphenyldicarboxylic acid. (See U.S. Pat. 4,263,466.)

As illustrated in the examples hereinbefore, the syntheses of dihydroxy polynuclear aromatics and diacids require considerable effort. An alternate route based on the direct alkylation of polynuclear aromatics would require fewer starting materials and fewer steps. For example, if biphenyl could be dialkylated with propylene selectively to p,p'-(diisopropyl)biphenyl, the latter could be converted directly to p,p'-dihydroxybiphenyl or to p,p'-biphenyldicarboxylic acid. Thus, the selective alkylation of polynuclear aromatic compounds would greatly simplify the syntheses of dihydroxyl polynuclear aromatics, diacids and hydroxy acids which are the building blocks for liquid crystal polymers.

It is known that aromatic hydrocarbons can be alkylated in the presence of acid-treated zeolite. U.S. Pat. No. 3,140,253 (1964) and U.S. Pat. No. 3,367,884 (1968) broadly teach the use of acid-treated mordenite for the alkylation of aromatic compounds. However, such alkylations are generally not selective with respect to site and number of substitutions.

More specifically, some of the prior art illustrates the use of acid-treated zeolites in the alkylation of polycyclic aromatic compounds. For example, U.S. Pat. No. 3,251,897 teaches the alkylation of naphthalene by acid-treated zeolites X, Y, and mordenite. However, the conversion of naphthalene is shown to be low, and the selectivity to di- and triisopropyl naphthalenes is low and otherwise unspecified. Japanese Patent 56-156,222 (1981) teaches the alkylation of biphenyl using silica alumina catalysts to give the monoalkylate in a para/meta ratio of 3/2. U.S. Pat. No. 4,480,142 (1984) discloses the alkylation of biphenyl in the presence of an acid-treated montmorillonite clay to yield 2-alkylbiphenyls as the major product.

Some of the prior art describes the use of acid-treated zeolites for the preparation of dialkylates high in para isomer content. For example, Japanese Patents 56-133,224 (1981) and 58-159,427 (1983) teach the use of acid extracted mordenite for the gas phase alkylation of benzene or monoalkylbenzenes to p-dialkylbenzenes. U.S. Pat. No. 4,283,573 (1981) discloses the alkylation of phenols by use of H-mordenites to produce p-alkyl phenols with placement of the phenolic moiety at the 2-position of the alkyl chain. U.S. Pat. No. 4,361,713 (1982) describes the treatment of numerous ZSM zeolite catalysts with a halogen-containing molecule, such as HCl, or $CCl_4$, and calcination at a temperature of from 300° C. to 600° C. to enhance the para-selective properties of such catalysts in the alkylation of benzene compounds. As illustrated with toluene, the conversion is taught to be low, while the selectivity to p-xylene is taught to be high.

Also recently, European Patent Application 0-202,752 (1986) teaches the alkylation of multi-ring aromatic hydrocarbons to alkylated derivatives high in $\beta$ and $\beta,\beta'$ isomers. The process involves contacting a multi-ring aromatic hydrocarbon with an alkylating agent other than an alcohol, such as an alkylaromatic hydrocarbon, in the presence of a medium- or large-pore, acid-treated zeolite.

Despite the numerous teachings in the prior art, there are few useful results of the alkylation of aromatic compounds, particularly polycyclic aromatic compounds, by zeolite catalysts. Such alkylations tend to give low conversion of the aromatic compound, and a low yield of the desirable p,p'-dialkylates or linear alkylates. A variety of by-products of low value is produced, making the separation and isolation of products difficult, if not impractical.

It would be highly desirable to find a process for the alkylation of aromatic compounds which would give high yields of disubstituted aromatic compounds enriched in the para alkylated isomers. Such a process would therefore find wide-spread utility in the synthesis of monomers for the preparation of thermotropic liquid crystal polymers.

SUMMARY OF THE INVENTION

In one aspect this invention is a process of alkylating an aromatic compound to a mixture of substituted aromatic compounds enriched in the para or linear alkylated isomers. (Hereinafter, the para or linear alkylated isomers are referred to simply as "linear" isomers.) The process comprises contacting an aromatic compound with an alkylating agent having from one to eight carbon atoms in the presence of a catalyst under conditions such that a mixture of alkylated aromatic compounds enriched in the linear alkylated isomers is formed. The catalyst is an acidic mordenite zeolite having a silica/alumina molar ratio of at least 15:1. In addition, the mordenite zeolite catalyst has a crystalline structure which is determined by X-ray diffraction to possess a Symmetry Index (SI), defined hereinafter, sufficient to increase the yield of linear alkylated aromatic isomers. Surprisingly, under the conditions of this process the conversion of the aromatic compound is higher than the conversions known heretofore. Moreover, under the conditions of this process the selectivity to the corresponding linear alkylated isomers is higher than known heretofore. Consequently, the yield of linear alkylated aromatic products is significantly higher than the yield of such products obtained by the alkylations disclosed in the prior art.

The linear alkylated aromatic compounds prepared by the process of this invention are useful intermediates in the preparation of monomers for thermotropic, liquid crystal polymers.

In another aspect, this invention is a novel catalyst composition comprising an acidic mordenite zeolite having a silica/alumina molar ratio of at least 50:1, a Symmetry Index (SI) as defined hereinafter of at least about 1.0, and a porosity such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å, a mesopore has a radius in the range of 10 Å to 100 Å, and a macropore has a radius in the range of 100 Å to 1000 Å.

In a further aspect, this invention is a process of preparing the aforementioned catalyst which process comprises first heating and then contacting with strong acid an acidic mordenite zeolite having a silica/alumina molar ratio less than 40:1 and a crystalline structure which is determined by X-ray diffraction to possess a Symmetry Index (SI) of from about 0.5 to about 1.0 under conditions sufficient to remove an amount of alumina sufficient to provide a silica/alumina molar ratio of at least 50:1.

DETAILED DESCRIPTION OF THE INVENTION

The aromatic compound which is employed in the process of this invention is any monocyclic or polycyclic aromatic compound. Any monocyclic aromatic compound is suitable provided that at least one of the para positions is unsubstituted. Such suitable compounds include benzene; linear and branched alkylbenzenes, such as toluene, ethylbenzene, n-propylbenzene, cumene, butylbenzenes including t-butylbenzene, phenylcyclohexane, o- and m-xylenes, and mesitylene: alkoxy-substituted benzenes, such as anisole and phenetole; polyalkylene oxide-substituted benzenes, such as polyethylene oxide phenyl ether, or polypropylene oxide phenyl ether: thiophenol and phenylalkyl thiols: halogenated benzenes, such as fluorobenzene, chlorobenzene, bromobenzene, iodobenzene, and their o- and m-dihalogenated homologues: and phenyl sulfides, such as methyl phenyl sulfide, or ethyl phenyl sulfide. Preferably, the monocyclic aromatic compound is unsubstituted, or substituted with no more than one substituent. More preferably, the monocyclic aromatic compound is represented by the formula:

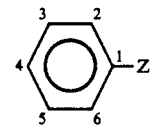

wherein Z is hydrogen, sulfhydryl, alkyl preferably of $C_{1-10}$ carbon atoms, aliphatic alkoxy or thioalkoxy of $C_{1-10}$ carbon atoms, fluoro, chloro, or bromo. Even more preferably, the monocyclic aromatic compound is benzene, cumene, t-butylbenzene, or anisole. Most preferably, the monocyclic aromatic compound is benzene or cumene.

The polycyclic aromatic compound of the invention is any aromatic compound containing a plurality of aromatic rings. The aromatic rings may be fused, like naphthalene, or non-fused ring assemblies, like biphenyl. The nomenclature and numbering of the fused and non-fused polycyclic compounds of this invention follow standard practice as found in Nomenclature of Organic Chemistry, International Union of Pure and Applied Chemistry, Butterworths, London, 1969, pp. 20–31 and 42–46. If fused, the aromatic compound preferably contains up to three rings. If non-fused, the polycyclic aromatic compound is represented by the preferred formula:

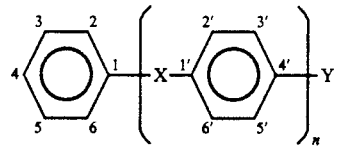

wherein n is a positive number from 1 to 3; Y is hydrogen, hydroxyl, sulfhydryl, alkyl preferably of $C_{1-10}$ carbon atoms, aliphatic alkoxy or thioalkoxy of $C_{1-10}$ carbon atoms, fluoro, chloro or bromo; and X may be absent or present. If absent, the phenyl rings are bonded at the 1,1' positions to each other. If present, X may be O, S, SO, $SO_2$, $CH_2$, $CH_2CH_2$, $CH_2CH_2CH_2$ or $CHCH_3$. In addition to being fused or non-fused, the aromatic rings may also be substituted or unsubstituted If substituted, the substituents may be at any position provided that at least one of the para (non-fused) or beta (fused) positions is unsubstituted. If the polycyclic aromatic compound is biphenyl, for example, the ortho (2,6) and meta (3,5) positions and one of the para (4) positions may be substituted. If the polycyclic aromatic hydrocarbon is naphthalene, the alpha (1,4,5,8) and beta (2,3,6,7) positions may be substituted, providing at least one beta position remains unsubstituted. The substituent may be a $C_1$–$C_2$ alkyl moiety, such as methyl or ethyl; fluoro; chloro; hydroxyl; or a $C_1$–$C_2$ alkoxy. However, if the substituent is "Y" as shown in the preferred formula, the substituent may include larger moieties as described hereinbefore. Preferably, the polycyclic aromatic compound is unsubstituted, or substituted with no greater than one $C_2$ moiety. More preferably, the polycyclic aromatic compound is unsubstituted. Examples of suitable polycyclic aromatic compounds which may be used in the invention are biphenyl, diphenyl ether, 4-hydroxy-1,1'-biphenyl, 4-phenoxy-1,1'-biphenyl, diphenylsulfide, terphenyl, tetraphenyl, diphenylmethane, 1,2-diphenylethane, 1,3-diphenylpropane, methylbiphenyls, ethylbiphenyls, 3- or 4-isopropylbiphenyl, naphthalene, methylnaphthalenes, ethylnaphthalenes, beta-isopropylnaphthalenes, and the like. Preferably, the polycyclic aromatic compound is a $C_{10}$–$C_{24}$ compound. More preferably, the polycyclic aromatic compound is an unsubstituted, fused or non-fused $C_{10-24}$ compound. Most preferably, the polycyclic aromatic hydrocarbon is biphenyl, diphenyl ether, or naphthalene.

The aromatic compound may be used neat in a liquid state, or dissolved in a suitable solvent. Preferably, the aromatic compound is used in a neat liquid state. If a solvent is employed, any inert solvent which solubilizes the aromatic compound and does not hinder the alkylation reaction may be used. The preferred solvent is 1,3,5-triisopropylbenzene or decalin.

The alkylating agent suitable for alkylating the above-identified aromatic compounds may be selected from a variety of materials, including monoolefins, diolefins, polyolefins, alcohols, alkyl halides, alkylsulfates, alkylphosphates, dialkylethers, and alkylaromatics. Exemplary of the monoolefins which may be employed in the process are ethylene, propylene, n-butene, isobutylene, 1-pentene, 1-hexene, cyclohexene, and 1-octene. 1,3-Butadiene is an example of a suitable diolefin. Alcohols, such as methanol, ethanol, isopropyl alcohol, isobutyl alcohol, pentyl alcohol, hexanol, and isohexanol, and alkyl halides, such as methyl chloride, isopropyl chloride, ethyl bromide, and methyl iodide are also suitable for use in the process. Alkylaromatics, such as xylenes, trimethylbenzenes, and the like, make suitable alkylating agents, as do ethers, such as dimethylether, diethylether, ethylpropylether, and diisopropylether. The preferred alkylating agent is an alkylating agent having from one to eight carbon atoms. The more preferred alkylating agent is a monoolefin, a diolefin or an alcohol having from one to eight carbon atoms. Even more preferred is an alkylating agent which is a monoolefin selected from the group consisting of propylene, n-butene, 1-hexene, cyclohexene, and 1-octene. Most preferably, the alkylating agent is propylene or n-butene.

The catalyst of the invention is an acid-modified zeolite with interconnecting twelve-ring and eight-ring channels. Zeolites have framework structures that are formally constructed from silicate and aluminate tetrahedra that share vertices. The tetrahedra may be linked to form pores or channels. The size of the pores is determined by the number of tetrahedra in the ring. Twelve-ring zeolites contain rings formed from twelve tetrahedra. Eight-ring zeolites contain rings formed from eight tetrahedra. The zeolites of this invention contain interconnecting twelve-ring and eight-ring channels. Examples of the zeolites suitable for use in this invention are mordenite, offretite and gmelinite. Mordenite-like zeolites, such as ECR-1 which is described in U.S. Pat. No. 4,657,748, and intergrowths of mordenite with other zeolites are also suitable catalysts: as are zeolites having a one-dimensional pore system with twelve-ring channels, such as type L or related zeolites. Preferably the catalyst is an acidic mordenite zeolite.

Mordenite is an aluminosilicate whose typical unit cell contents are assigned the formula $Na_8[(AlO_2)_8(SiO_2)_{40}24\ H_2O]$. Mordenite is the most siliceous natural zeolite with a silicon/aluminum mole ratio (Si/Al) of about 5/1. The dimensions of the twelve-ring pores are about $6.7 \times 7.0$ Å; the dimensions of the eight-ring pores are about $2.9 \times 5.7$ Å. The structure and properties of mordenite zeolite are described in *Zeolite Molecular Sieves*, by Donald W. Breck (John Wiley & Sons, 1974), at pages 122–124 and 162–163, which is incorporated herein by reference.

The catalyst of this invention is prepared from a mordenite zeolite typically containing cations of the alkali or alkaline earth metals, or alternatively ammonium ions. Preferably, the catalyst of the invention is prepared from a sodium mordenite zeolite: even more preferably, from a sodium mordenite zeolite having a Symmetry Index less than about 1.0. The Symmetry Index is a dimensionless number obtained from the X-ray diffraction pattern of the sodium mordenite being measured in the hydrated form. Standard techniques are employed to obtain the X-ray data. The radiation is the $K\alpha_1$ line of copper, and a Philips Electronics spectrometer is used. The mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," *Molecular Sieves*, J. W. Meier and J. B. Uytterhoeven, eds., Advances in Chemistry Series, 121, 1973, pp. 52–65. The Symmetry Index is defined as the sum of the peak heights of the [111] (13.45, $2\theta$) and [241] (23.17 $2\theta$) reflections divided by the peak height of the [350] (26.25 $2\theta$) reflection. Preferably, the Symmetry Index of the sodium mordenite ranges from about 0.50 to about 1.0. More preferably, the Symmetry Index of the sodium mordenite ranges from about 0.60 to about 1.0.

Four ordered crystalline structures have been proposed to describe the X-ray diffraction data available for natural and synthetic mordenite zeolites. (J. D. Sherman and J. M. Bennett, op.cit., p. 53.) The symmetries of these four structures are Cmcm, Cmmm, Imcm, and Immm as these terms are defined by N. F. M. Henry and K. Lonsdale in *International Tables for X-ray Crystallography*, 3rd Ed., Volume 1, Kynoch Press (1969). X-ray diffraction data indicate that mordenites are either physical admixtures or intergrowths of the Cmmm, Imcm, or Immm structures with the Cmcm structure. Thus, mordenites can be generally described as having a crystalline structure comprising a matrix of Cmcm symmetry having dispersed therein domains of Cmmm, Imcm, or Immm symmetry, or mixtures thereof. Preferably, the mordenite of this invention has a crystalline structure comprising a matrix of Cmcm symmetry having dispersed therein domains of Cmmm symmetry. The Symmetry Index is related to the symmetries of the crystals present in the mordenite sample. A Symmetry Index in the range from about 0.60 to about 1.0 provides the optimum sodium mordenite as starting material for the process of this invention.

The crystallite size of the original sodium mordenite may be any size which yields a catalyst selective for alkylated aromatic compounds enriched in the para isomers. Typically, the crystallite size may be in the range from about 500 Å to about 5000 Å. Preferably, the crystallite size is in the range from about 500 Å to about 2000 Å; more preferably, from about 800 Å to about 1500 Å. Generally, the crystallites form aggregates which may be used as such or bound into larger particles for the process of this invention. For example, extrudate can be made for a packed-bed reactor by compressing the aggregates into binderless particles of suitable sizes. Alternatively, the extrudate can be made via use of binders well-known to those in the art. The preferred particle size ranges from about 1 micron ($\mu$) to about 20 $\mu$.

The original sodium mordenite zeolite described hereinabove, or its equivalent, is treated to obtain the catalyst of the invention for use in the alkylation process. The treatment involves contacting the mordenite with acid. Preferably, the treatment involves contacting the mordenite with acid, calcining the acid-treated mordenite, and further contacting the calcined mordenite with strong acid.

The initial acid treatment serves to remove most of the sodium ions, or their equivalents, from the original mordenite. The treatment may remove a portion of the aluminum ions as well. Inorganic acids and organic acids are suitable compounds from which the hydrogen ions are obtained for the acid treatment. Examples of such acids are hydrochloric acid, hydrobromic acid, sulfuric acid, phosphoric acid, nitric acid, acetic acid, oxalic acid, and the like. Inorganic acids are the preferred source of hydrogen ions; with hydrochloric, nitric and phosphoric acids being more preferred and hydrochloric acid being most preferred. An equally acceptable initial treatment involves ion exchange with ammonium salts, such as ammonium chloride. By this method the sodium ions, or their equivalents, are removed, but the aluminum ions are not displaced. On heating the ammonium exchanged mordenite, ammonia is given off and the mordenite is converted to the acid form.

Typically, in the initial acid treatment the original sodium mordenite is slurried with an aqueous solution of the acid. The acid solution may have any concentration, providing the catalyst obtained possesses the properties and activity of the catalyst of this invention, these being described hereinafter. Preferably, the concentration of the aqueous acid solution is in the range from about 0.01N to about 6N; more preferably in the range from about 0.5N to about 3.0N. The relative quantities of aqueous acid solution to mordenite solid which are employed may vary. Typically, the ratio is less than about 15 cc acid solution per gram mordenite solid. Preferably, the ratio is in the range from about 5 cc acid solution per gram mordenite solid to about 10 cc acid solution per gram mordenite solid. The temperature and the duration of the contact of the mordenite with the acid solution may also vary. Preferably, the mordenite is contacted with the acid at a temperature in the range from about 10° C. to about 100° C. Generally, the contact time between the acid solution and the mordenite may vary from about 5 minutes to about several hours. It is important that there be sufficient time for the acid solution to contact all of the mordenite particles. Preferably, the contact time is from about 5 minutes to about 60 minutes. The acid extraction, as described herein, may be repeated if desired. Afterwards, the mordenite is washed in water one or more times in order to rinse away soluble species from the mordenite. Preferably, the water wash is carried out at ambient temperature. Optionally, subsequent to the water wash the mordenite is dried in air at a temperature in the range from about 20° C. to about 150° C.

In the preferred treatment, following the exchange with acid and drying in air, the acidic mordenite zeolite is calcined in air or heated in an inert atmosphere, such as nitrogen. It is believed that this heat treatment dislocates a portion of the aluminum from the zeolite framework: however, such a theory should not be taken as limiting of the scope of the invention. Typically, the temperature of the calcination or heating may range from about 250° C. to about 950° C. Preferably, the temperature of the calcination or heating is in the range from about 300° C. to about 800° C. More preferably, the temperature is in the range from about 400° C. to about 750° C. Most preferably, the temperature is from about 500° C. to about 700° C.

After calcining the acid-treated mordenite described hereinabove, the mordenite is subjected to an additional acid treatment for the purpose of further dealumination. The second acid treatment comprises contacting the calcined mordenite with a strong acid under conditions sufficient to produce the acidic mordenite catalyst of this invention. For the purposes of this invention a "strong" acid is defined as an acid which reacts essentially completely with the solvent to give the conjugate acid of the solvent. For example, if gaseous hydrogen chloride is dissolved in water, the acid-base reaction is complete to give the conjugate acid $H_3O^+$ and $Cl^-$. Preferably, the strong acid is an inorganic acid. More preferably, the strong acid is nitric acid, hydrochloric acid, or sulfuric acid. Most preferably, the strong acid is nitric acid. The concentration of the strong acid will vary depending on the acid selected. In general, the acid is employed in an aqueous solution of any concentration which provides for the extraction of aluminum from the calcined acidic mordenite, as described hereinafter. With nitric acid, for example, the concentration of the acid in the aqueous solution is preferably in the range from about 2N to about 15N. More preferably, the concentration of the acid is in the range from about 4N to about 12N. Most preferably, the concentration of the acid is in the range from about 6N to about 8N. The aqueous acid solution and the calcined mordenite are contacted in any ratio that provides the catalyst of the invention. Preferably, the ratio of aqueous acid solution to mordenite is in the range from about 3 cc acid solution per gram mordenite to about 10 cc acid solution per gram mordenite. More preferably, the ratio is about 5 cc acid solution per gram mordenite. The temperature and the duration of the contact may vary depending on the acid selected. Preferably, the mordenite is contacted with the acid solution at a temperature in the range from about ambient temperature taken as 22° C. to about 220° C. More preferably, the mordenite and the acid are contacted at a temperature which allows for boiling of the aqueous acid under atmospheric conditions. Preferably, the duration of the contact is from about 1 hour to about 6 hours; more preferably, from about 1 hour to about 3 hours; most preferably, for about 2 hours. When the contacting with strong acid is complete, the mordenite is filtered and washed repeatedly with water until the washings are acid-free. Preferably, the washed mordenite is heat treated and contacted with strong acid more than once. Lastly, the washed acidic mordenite zeolite is dried for several hours at a temperature in the range from about 100° C. to about 150° C. to remove physically adsorbed water.

The dried acidic mordenite is activated by heating for about 2 hours at a temperature in the range from about 300° C. to about 700° C. This activation may drive off more strongly bound water and any residual adsorbates.

After the original sodium mordenite is treated with acid, calcined, and retreated with strong acid according to the process of this invention, an acidic mordenite catalyst is obtained which is capable of converting an aromatic compound in a high conversion to a mixture of substituted aromatic compounds enriched in the para or linear alkylated isomers. This catalyst exhibits special characteristics by which it may be identified, specifically, the silica/alumina molar ratio, and the Symmetry Index and porosity as defined hereinafter.

As a result of the acid extractions, the silica/alumina molar ratio ($SiO_2/Al_2O_3$) of the acidic mordenite catalyst is increased over that of the original sodium mordenite. Specifically, the acid-treated mordenite catalyst has a silica/alumina molar ratio of at least 15:1. Preferably, the silica/alumina molar ratio is at least about 50:1; more preferably, at least about 150:1. Most preferably, the silica/alumina molar ratio ranges from about 200:1 to about 1000:1.

As a further result of the acid extractions and calcination, the Symmetry Index of the mordenite catalyst is increased over that of the original mordenite. The Symmetry Index is as defined hereinbefore. Since the Symmetry Index is derived from X-ray data, the Index is related to the proportion of Cmcm, and Cmmm, Imcm, or Immm symmetries present in the catalyst. The increase in the Symmetry Index is indicative of the enrichment of the catalyst in the Cmcm component. For polycyclic aromatic compounds a Symmetry Index of at least about 1.0 results in catalysts capable of achieving high yields of the linear alkylated polycyclic aromatic compounds. Preferably, the Symmetry Index ranges from about 1.0 to about 2.3. More preferred is a Symmetry Index in the range from about 1.2 to about 2 3, most preferably, from about 1.5 to about 2.0. For monocyclic aromatic compounds a Symmetry Index of at least about 1.5 results in a high yield of the linear alkylated monocyclic aromatic compound. Preferably, the Symmetry Index is in the range from about 1.5 to about 2.3, more preferably, in the range from about 1.7 to about 2.2.

A third property of the acidic mordenite catalyst, by which it is identified, is the porosity. All zeolites possess pores which form as a natural consequence of zeolite crystal growth. New pores or modifications of existing pores can occur on treating the zeolites, for example, with heat or acid as in the process of this invention. Typically, pores are classified into micropores, mesopores and macropores. For the purposes of this invention a micropore is defined as having a radius in the range from about 3 Angstrom units (3 Å) to 10 Å. Likewise, a mesopore is defined as having a radius in the range from 10 Å to 100 Å, while a macropore is defined as having a radius from 100 Å to 1000 Å. After calcination and strong acid treatment, the acidic mordenite catalyst of this invention possesses micro-, meso- and macropores. The porosity of the catalyst may be distinguished by the total pore volume defined as the sum of the volumes of the micro-, meso-, and macropores per gram catalyst. A catalyst of this invention has a total pore volume sufficient to provide a high yield of para alkylated isomers in the alkylation of an aromatic compound. Preferably, the total pore volume is in the range from about 0.18 cc/g to about 0.45 cc/g. The porosity may be further distinguished by the relative distribution of meso- and macropores, as found in the ratio of the combined meso- and macropore volume to the total pore volume. A catalyst of this invention has a ratio of combined meso- and macropore volume to total pore volume sufficient to provide a high yield of para alkylated isomers in the alkylation of an aromatic compound. Preferably, the ratio of the combined meso- and macropore volume to total pore volume is in the range from about 0.25 to about 0.75.

The measurement of the porosity, described hereinabove, is derived from surface area and pore volume measurements of mordenite powders obtained on any suitable instrument, such as a Quantachrome Digisorb-6 unit, using nitrogen as the adsorbate at the boiling point of nitrogen, 77° K. The total pore volume ($V_T$) is derived from the amount of nitrogen adsorbed at a relative pressure close to unity. It is accepted that this volume constitutes pores of less than 1000 Å in radius. As stated earlier, for the purposes of this invention pores with radius of 10 Å or less are called micropores. Pores with radius from 10 Å to 100 Å are called mesopores, and pores with radius from 100 Å to 1000 Å are called macropores. Pores with radius in the 10 Å to 1000 Å range are known in the literature as "transitional pores". The micropore volume ($V_m$) in the presence of "transitional pores" is obtained by the t-method. The difference between the total pore volume and the micropore volume is the transitional pore volume, ($V_t = V_T - V_m$). The cumulative pore distribution in the transitional pore range is used to calculate the relative volume contributions of mesopores and macropores. For example, the mesopore volume is calculated by multiplying the transitional pore volume by the fraction of the cumulative pore volume from 10 Å to 100 Å, ($V_{me} = V_t f_{me}$). The macropore volume is then simply obtained by subtracting the mesopore volume from the transitional volume, ($V_{ma} = V_t - V_{me}$). This approach ensures that the equation $V_T = V_m + V_{me} + V_{ma}$ is satisfied. The adsorption isotherms obtained for the mordenite catalysts of this invention are of Type I, which are described by the Langmuir equation. The Langmuir surface are is obtained from such equation. The methods used to obtain surface areas and pore volumes are described by S. Lowell in *Introduction to Powder Surface Area* (John Wiley and Sons, 1979), or in the manuals provided with the Digisorb-6 instrument made by the Quantachrome Corporation.

The acidic mordenite catalyst, identified hereinabove, is capable of adsorbing biphenyl into the intracrystalline pore system, and conversely desorbing biphenyl. Biphenyl adsorption is effected by exposing the acidic mordenite to biphenyl vapors at 100° C. for a time sufficient to obtain near constant weight. Preferably, the adsorption capacity of the acidic mordenite for biphenyl is about 5 weight percent. More preferably, the capacity is about 10 weight percent. Biphenyl desorption is effected by heating the mordenite-biphenyl sample in a dynamic helium atmosphere from 25° C. to about 1000° C. at a heating rate of about 10° C./minute. The desorption of biphenyl may be followed experimentally by thermal gravimetric analysis combined with gas phase chromatography and mass spectrometry (TGA-GC-MS). It is found that weakly adsorbed biphenyl produces a weight loss at temperatures below about 300° C.; whereas, strongly adsorbed biphenyl produces a weight loss at temperatures from about 300° C. to as high as 1000° C. The amount of strongly adsorbed biphenyl is estimated by subtracting the amount of weakly adsorbed biphenyl from the total amount of biphenyl desorbed from the sample. A fully treated mordenite catalyst of this invention exhibits a sharp weight loss at temperatures below about 300° C., and little or no weight loss from 300° C. to 1000° C. In contrast, acid-exchanged mordenite exhibits a sharp weight loss at temperatures below about 300° C., and a second weight loss starting at about 300° C. and extending to 1000° C. It is believed that the weakly adsorbed biphenyl is located in sites from which there is relatively easy exit: whereas the strongly adsorbed biphenyl is located in sites from which there is relatively difficult exit. Thus, the acidic mordenite catalyst of this invention provides easy access and egress to adsorbed biphenyl. Such a theory, however, should not be construed to be binding or limiting of the scope of the invention.

The ratio of the aromatic compound to catalyst may be any weight ratio which produces alkylates enriched in the para-substituted isomers. Preferably, the weight ratio of aromatic compound to catalyst is in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the yield of para-substituted products may be reduced. Above the preferred upper limit of 2000:1, the conversion of the aromatic compound may be low.

The ratio of aromatic compound to alkylating agent may vary depending on the number of open para or beta positions on the aromatic compound. For example, if the aromatic compound to be alkylated has only one open para position, the ratio of alkylating agent to aromatic compound is 1:1. If the aromatic compound has two open para positions, the ratio is 2:1. The alkylating agent may be introduced to the reaction all at once, as in the case of a liquid alkylating reagent. Alternatively, the alkylating agent may be introduced to the reaction on demand until the desired degree of conversion is achieved, as in the case of a gaseous alkylating agent which is continuously fed into the reactor.

The contacting of the aromatic compound with the alkylating agent in the presence of the catalyst may occur in a reactor of any configuration. Batch-type and continuous reactors, such as fixed-bed, slurry bed, fluidized bed, catalytic distillation, or countercurrent reactors, are suitable configurations for the contact. Preferably, the reactor is fit with a means for observing and controlling the temperature of the reaction, a means for observing and measuring the pressure of the reaction, and optionally a means for agitating the reactants. The aromatic compound may be in the molten, liquid form or in solution. The alkylating agent may be introduced in the liquid or gaseous state, and may be added all at once at the start of the reaction, or fed continuously on demand from the reaction. The catalyst may be used in various forms, such as a fixed-bed, moving bed, fluidized bed, in suspension in the liquid reaction mixture, or in a reactive distillation column.

The contacting of the reactants in the presence of the catalyst may occur at any temperature or pressure which will produce as the major products the substituted aromatic compounds enriched in the para alkylated isomers. Preferably, the temperature is in the range from about 100° C. to about 400° C. More preferably, the temperature is in the range from about 125° C. to 300° C. Most preferably, the temperature is in the range from about 150° C. to about 250° C. Below the preferred lower limit of 100° C. the reaction proceeds slowly. Above the preferred upper limit of 400° C., the alkyl groups may scramble upsetting the selectivity for the para isomers. Preferably, the pressure in the reactor is in the range from about 10 psig to about 500 psig. More preferably, the pressure is in the range from about 30 psig to about 300 psig. Most preferably, the pressure is in the range from about 70 psig to about 200 psig. Below the preferred lower limit of 10 psig the catalyst begins to lose selectivity for para isomers. Above the preferred upper limit of 500 psig the preferred olefin alkylating agent will polymerize severely.

The aromatic compound, alkylating agent, and catalyst are contacted for a time sufficient to convert the aromatic compound to alkylated products, and sufficient to produce the desired yield of para-alkylated aromatic compounds. Generally, the contact time will depend on other reaction conditions, such as temperature, pressure and reagent/catalyst ratios. In a typical stirred batch reactor, for example, the reaction time is preferably in the range from about 0.1 hour to about 40 hours. More preferably, the reaction time is in the range from about 0.5 hour to about 20 hours.

The products of this invention include a mixture of alkylated aromatic compounds enriched in the para or linear alkylated isomers. The para or linear alkylated isomers are those in which the alkyl group(s) is(are) attached at the ends of the molecule, thereby yielding the product of smallest critical diameter. In the alkylation of benzene, for example, the enriched product is the para-dialkylate (1,4-dialkylate). In the alkylation of biphenyl, for example, one such enriched product is the para,para'-dialkylate (4,4'-dialkylate). Likewise, in the alkylation of terphenyl, one such enriched product is the para',para''-dialkylate (4',4''-dialkylate). In the alkylation of naphthalene, a fused ring system, one such enriched product is the linear 2,6-dialkylate. Such products provide the smallest critical diameter to the alkylated molecule, and are also referred to as the "linear" alkylated products. All other alkylated products yield molecules of larger critical diameter.

For the purposes of this invention, the term "conversion" refers to the mole percent of aromatic compound which reacts to form alkylated products. Typically, in the batch reaction, the conversion achieved in the practice of this invention is at least about 20 mole percent. Preferably, the conversion is at least about 50 mole percent, more preferably at least about 65 mole percent. Even more preferably, the conversion is at least about 80 mole percent. Most preferably, the conversion is at least about 95 mole percent.

Likewise, the term "selectivity" refers to the mole percent of reacted aromatic compound which is converted to a specific alkylated product. For example, in the practice of this invention biphenyl is converted to alkylates enriched in the p,p'-dialkylate, 4,4'-di(1-methylethyl)-1,1'-biphenyl. Smaller amounts of the 3- and 4-monoalkylated isomers, and the 3,4'-dialkylated isomer are obtained. Even smaller amounts of the 2-monoalkylated isomer and the dialkylates in which both alkyls are attached to one ring are obtained. Typically, the selectivity to total dialkylated biphenyls ranges from about 25 mole percent to about 80 mole percent. Typically, the selectivity to p,p'-dialkylated biphenyl achieved in the practice of this invention is at least about 20 mole percent. Preferably, the selectivity to the p,p'-dialkylated biphenyl is at least about 40 mole percent. More preferably, the selectivity is at least about 50 mole percent. Most preferably, the selectivity is at least about 70 mole percent. More generally, the selectivity to linear alkylates achieved in the practice of this invention is at least about 20 mole percent. Preferably, the selectivity to linear alkylates is at least about 40 mole percent, more preferably, at least about 50 mole percent, most preferably at least about 70 mole percent.

The selectivity for p,p'-dialkylates may also be expressed as the product $100 \times p,p'/\Sigma Di \times \Sigma Di/TA$. The first factor is the ratio $p,p'/\Sigma Di$, wherein p,p' represents the moles of p,p'-dialkylated isomer and $\Sigma Di$ represents the total number of moles of dialkylated isomers. This ratio indicates the fraction of the total dialkylates which are the p,p' isomer. Typically, this ratio, expressed as a percentage, is at least about 40 mole percent. Preferably, $p,p'/\Sigma Di$ is at least about 60 mole percent: more preferably, at least about 70 mole percent: most preferably, greater than about 80 mole percent. The second factor is the ratio $\Sigma Di/TA$, wherein $\Sigma Di$ is defined as above and TA is the total number of moles of all alkylated products. This ratio indicates the fraction of all alkylated products which are dialkylates. Typically, this ratio, expressed as a percentage, is at least about 15 mole percent. Preferably, $\Sigma Di/TA$ is at least about 30 mole percent; more preferably, at least about 50 mole percent; most preferably, at least about 70 mole percent.

The concept of simultaneous high conversion and high selectivity to the linear alkylated aromatic compounds may be expressed conveniently in terms of yield. For the purposes of the present invention, the term "yield" refers to the numerical product of conversion and selectivity. For example, a process according to the present invention operating at a conversion of 0.982, or 98.2 percent, and a selectivity to para alkylated isomer of 0.650, or 65 percent, would have a yield of the para isomer of 0.638, or 63.8 percent, which is the numerical product of 0.982 and 0.650. Typically, the yield of total dialkylates achieved in the process of this invention is at least about 20 mole percent; preferably, at least about 45 mole percent; more preferably, at least about 75 mole percent. In contrast to the alkylations of the prior art, the process of the present invention may be operated to give higher yields of the linear alkylated isomers. Typical yields of the linear alkylated isomers are at least about 10 mole percent. Preferably, the yield of linear alkylated isomers is at least about 20 mole percent, more preferably, at least about 40 mole percent, even more preferably, at least about 55 mole percent, and most preferably, at least about 70 mole percent.

Following the alkylation of the aromatic compound, the product mixture may be separated by standard techniques, such as distillation, melt crystallization, or solvent-assisted recrystallization. In the case of a product mixture containing biphenyl and its propylated derivatives, distillation is a convenient method of separating the products. Biphenyl may be removed in a first distillation column; 3-(1-methylethyl)-1,1'-biphenyl, 4-(1-methylethyl)-1,1'-biphenyl, and 3,4'-di(1-methylethyl)-1,1'-biphenyl may be removed in a second distillation column. The bottoms may be transported to a third distillation column from which enriched 4,4'-di(1-methylethyl)-1,1'-biphenyl is distilled off. The final residuals contain small amounts of triisopropylbiphenyls. 2-, 3-, and 4-Monoalkylates and residual dialkylates may be used as chemical intermediates, as high temperature heat-transfer fluids, or as solvents. Alternatively, these by-products and any triisopropylbiphenyls may be converted via transalkylation with benzene to valuable biphenyl and cumene. The p,p'-dialkylate fraction may be upgraded to a purity greater than 99 weight percent by melt recrystallization.

Specific Embodiments

The following examples are given to illustrate the catalyst and the process of this invention and should not be construed as limiting its scope. All percentages in the examples are mole percent unless otherwise indicated.

EXAMPLE 1

Preparation of Acidic Mordenite Catalyst

A crystalline sodium mordenite is selected with the following properties: a $SiO_2/Al_2O_3$ ratio of 15, a $SiO_2/Na_2O$ ratio of 15, a crystallite size of 1000 Å with aggregates ranging in size from 1 micron to 20 microns, a Symmetry Index of 0.97 as determined by X-ray diffraction on a Philips Electronic spectrometer using the $K\alpha 1$ line of copper; and a Langmuir surface area of 303 m$^2$/g. The total pore volume of the sodium mordenite, determined on a Quantachrome Digisorb-6 unit using nitrogen as the adsorbate at 77° K., is found to be 0.194 cc/g. The micropore volume, as determined by a t-plot, is found to be 0.046 cc/g. The transitional pore volume, given by the difference (0.194 cc/g-0.046 cc/g), equals 0.148 cc/g, of which 0.083 cc/g are due to mesopores, and 0.065 cc/g are due to macropores.

The sodium mordenite (200 g), described hereinabove, is converted to acidic mordenite via exchange with 2000 ml of 1N aqueous hydrochloric acid at room temperature for thirty minutes. The mordenite-acid slurry is maintained homogeneous by agitation during this period, after which the acid-treated mordenite is isolated by filtration. The filtered solid is washed by suspension in 2000 ml of water, refiltered, and dried in air at 110° C. The dried solid is heated to 700° C. in flowing air for 2 hours. The heated solid is cooled to room temperature in air. The heat-treated acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. to yield the acidic mordenite catalyst of the invention. Analysis of said catalyst by previously described methods gives the following results: a $SiO_2/Al_2O_3$ ratio of 256/1; a $SiO_2/Na_2O$ ratio of 3732/1; a Symmetry Index of 1.17; a Langmuir surface area of 673 m$^2$/g, a total pore volume of 0.408 cc/g; a micropore volume of 0.208 cc/g; a mesopore volume of 0.068 cc/g; a macropore volume of 0.132 cc/g; and a ratio of combined meso- and macropore volume to total pore volume of 0.49. The catalyst is activated by heating in air at 700° C. for 2 hours.

EXAMPLE 2

Alkylation of Biphenyl

A one-liter stirred tank reactor is equipped with a means for observing and controlling temperature, a means for observing and controlling pressure, and a means for agitating the contents of the reactor. Biphenyl (500 g) and the acidic mordenite catalyst of Example 1 (10 g) are added to the reactor. The reactor is sealed and purged with gaseous propylene. The reactor is pressurized with gaseous propylene to 120 psig, and then heated to 250° C. The reactor contents are agitated at 2000 rpm. As propylene is consumed by the reaction, additional propylene is continuously fed to the reactor so as to maintain a total pressure of 120 psig. The reactor is sampled at 4 hours and 9 hours, and the products are analyzed by gas-phase chromatography. The results are set forth in Table I.

TABLE I

| Example | Time (hr) | % Conversion | % p,p' Yield | % p,p'/ΣDi | % ΣDi/TA |
|---------|-----------|--------------|--------------|------------|----------|
| 2(a)    | 4         | 84           | 45           | 86         | 62       |
| 2(b)    | 9         | 98           | 60           | 86         | 71       |

"Di" represents dialkylated biphenyls. "ΣDi" is the sum of the moles of p,p', p,m' and m,m' dialkylates. "TA" represents total moles of alkylbiphenyls.

EXAMPLE 3

Preparation of Acidic Mordenite Catalyst

A crystalline sodium mordenite is selected having a $SiO_2/Al_2O_3$ mole ratio of 19.0, and a crystalline size of 1000 Å as aggregates of 2 to 20 microns. The Langmuir surface area and porosity of the sodium mordenite are determined on a Quantachrome Digisorb-6 unit and are found to be the following: Langmuir surface area 378 m²/g; a total pore volume of 0.239 cc/g; a micropore volume of 0.100 cc/g; a mesopore volume of 0.054 cc/g; and a macropore volume of 0.085 cc/g. The Symmetry Index is determined by X-ray diffraction to be 1.26.

The sodium mordenite, described hereinabove, is made into a slurry by adding 200 g of said mordenite to 2000 ml of 1N aqueous hydrochloric acid solution. The slurry is maintained homogeneous by agitation with a magnetic stirring bar. After 30 minutes the acid-treated mordenite is filtered. The acid treatment is repeated twice. The filtered solids are washed by suspension in 2000 ml of deionized water for 30 minutes at room temperature. The washed, acid-exchanged mordenite is filtered. The washing procedure is repeated twice. After the last wash the filtered solids are dried at 110° C. in air overnight to yield 180 g of dried, acidic mordenite. The resulting solid is an acidic mordenite catalyst having a $SiO_2/Al_2O_3$ ratio of 19.6, a Symmetry Index of 1.69, a Langmuir surface area of 600 m²/g, a total pore volume of 0.332 cc/g, a micropore volume of 0.189 cc/g, a mesopore volume of 0.042 cc/g, a macropore volume of 0.101 cc/g, and a combined meso- and macropore volume of 0.430. The catalyst is activated by heating in air at 700° C. for 2 hours.

EXAMPLES 4–8

Alkylation of Biphenyl

A series of reactions is conducted with the catalyst of Example 3 according to the procedure of Example 2, except for varying the alkylating agent. Example 4: propylene is fed into the reactor as a gas at a pressure of 120 psig. Example 5: 1-butene is fed into the reactor as a gas at a pressure of 100 psig. Example 6: 2-butene is fed into the reactor under a vapor pressure of 60 psig. Examples 7 and 8: 1-pentene and 1-hexene, respectively, are fed into the reactor as a liquid with an olefin to biphenyl ratio of about 4. The reaction temperature in all runs is 250° C.; and the reaction time in all runs is 20 hours. The results are set forth in Table II.

TABLE II

| Example | Olefin    | % Conversion | % p,p' Yield | % p,p'/ΣDi | % ΣDi/TA |
|---------|-----------|--------------|--------------|------------|----------|
| 4       | propylene | 90           | 53.7         | 86.2       | 62.3     |
| 5       | 1-butene  | 97.8         | 68.2         | 94         | 70       |
| 6       | 2-butenes | 92           | 50.4         | 83         | 66       |
| 7       | 1-pentene | 96           | 38           | 63         | 63       |
| 8       | 1-hexene  | 91.5         | 27           | 50         | 35       |

"Di" represents dialkylated biphenyls. "ΣDi" is the sum of the moles of p,p', p,m' and m,m' dialkylates. "TA" represents the moles of total alkylbiphenyls.

EXAMPLE 9

Alkylation of Biphenyl

Biphenyl (50 g) and isopropanol (50 cc) are dissolved in 200 cc of 1,3,5-triisopropylbenzene, and the solution is contacted with the catalyst of Example 3 (10 g) at a temperature of 250° C. for 24 hours. Analysis of the product mixture gives a conversion of 36 percent and a yield of p,p'-dialkylate of 6.1 percent. The p,p'/ΣDi factor is 69 percent, and ΣDi/TA factor is 24.6 percent.

EXAMPLE 10

Alkylation of Diphenyl Ether

Diphenyl ether (500 g) and the catalyst of Example 1 (10 g) are contacted with propylene at a pressure of 100 psig and a temperature of 250° C. for 20 hours. Analysis of the product mixture gives a conversion of 98.7 percent and a yield of p,p'-dialkylate of 63.4 percent. The p,p'/ΣDi factor is 82 percent, and the ΣDi/TA factor is 80 percent.

EXAMPLE 11

Alkylation of Naphthalene

Naphthalene (500 g) and the catalyst of Example 1 (10 g) are added to the reactor of Example 2. Propylene gas is added to the reactor to a total pressure of 120 psig. The reactor is heated at 250° C. for 20 hours, while maintaining the pressure at 120 psig. Analysis of the products by gas chromatography gives a conversion of 97.3 percent, a yield of 2,6'-dialkylate of 42.7 percent, and a yield of 2,7'-dialkylate of 20 percent. The 2,6'/ΣDi factor is 64 percent, and the ΣDi/TA factor is 68 percent, wherein "ΣDi" represents the total moles of dialkylated naphthalenes and "TA" represents the total moles of alkylated products.

EXAMPLE 12

Alkylation of Diphenylmethane

Diphenylmethane (500 g) and the catalyst of Example 1 (10 g) are contacted with propylene at a temperature of 250° C. and a pressure of 120 psig for 20 hours. Analysis of the product mixture gives a conversion of 98.5 percent, a yield of p,m'-dialkylate of 43.8 percent, and a yield of p,p'-dialkylate of 25.5 percent. The p,p'/ΣDi factor is 34 percent, and the ΣDi/TA factor is 77 percent.

EXAMPLE 13

Alkylation of 4-Hydroxy-1,1'-biphenyl

4-Hydroxy-1,1'-biphenyl (250 g), cyclohexene (250 g), and the catalyst of Example 3 (10 g) are heated at 250° C. under 1 atmosphere of nitrogen gas for three days. Analysis of the product mixture gives a conversion of 86.7 percent and a yield of 4-hydroxy-4'-cyclohexyl-1,1'-biphenyl of 55.3 percent.

EXAMPLE 14

Preparation of Catalyst

A crystalline acidic mordenite is selected with the following properties: a $SiO_2/Al_2O_3$ ratio of 200, a crystallite size of about 1000 Å with aggregates ranging in size from about 1 micron to about 20 microns, a Symmetry Index of 1.82 as determined by X-ray diffraction on a Philips Electronic spectrometer using the $K\alpha 1$ line of copper; and a Langmuir surface area of 680 m$^2$/g. The porosity, determined on a Quantachrome Digilab-6 unit, is found to be the following: total pore volume of 0.320 cc/g; micropore volume of 0.203 cc/g; mesopore volume of 0.049 cc/g; macropore volume of 0.068 cc/g; and a ratio of combined meso- and macropore volume to total pore volume of 0.366.

The acidic mordenite solid (100 g), described hereinabove, is heated at 700° C. in flowing air for 2 hours, then cooled to room temperature in air. The cooled acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. The treatment with heat at 700° C. and the treatment with 6N nitric acid are repeated one more time. The resulting solid is washed with water until free of residual acid and dried in air at 100° C. to yield the acidic mordenite catalyst of the invention. Analysis of the catalyst by previously described methods gives the following results: a Symmetry Index of 2.07; a Langmuir surface area of 389 m$^2$/g; a total pore volume of 0.376 cc/g; a micropore volume of 0.149 cc/g; a mesopore volume of 0.075 cc/g; a macropore volume of 0.152 cc/g; and a combined ratio of mesopore and macropore volume to total pore volume of 0.604. The catalyst is activated by heating in air at 700° C. for 2 hours.

EXAMPLE 15

Alkylation of Biphenyl

Biphenyl (500 g) and the catalyst of Example 14 (10 g) are contacted with propylene at a pressure of 120 psig and a temperature of 250° C. Analysis of the product mixture at 2 hours gives a biphenyl conversion of 85 percent and a yield of p,p'-dialkylate of 60 percent. The p,p'/ΣDi factor is 86 percent, and ΣDi/TA factor is 70 percent. Analysis of the product mixture at 20 hours gives a biphenyl conversion of 98 percent and a yield of p,p'-dialkylate of 68 percent. The p,p'/ΣDi factor is 86 percent, and ΣDi/TA factor is 80 percent.

EXAMPLE 16

Preparation of Catalyst

A crystalline acidic mordenite is selected with the following properties: a $SiO_2/Al_2O_3$ ratio of 175, a crystallite size of about 1000 Å with aggregates ranging in size from about 5 microns to about 20 microns, a Symmetry Index of 2.08 as determined by X-ray diffraction on a Philips Electronic spectrometer using the $K\alpha 1$ line of copper; and a Langmuir surface area of 653 m$^2$/g. The porosity, determined on a Quantachrome Digilab-6 unit, is found to be the following: total pore volume of 0.44 cc/g; micropore volume of 0.18 cc/g; mesopore volume of 0.06 cc/g; macropore volume of 0.20 cc/g; and a ratio of combined meso- and macropore volume to total pore volume of 0.59.

The acidic mordenite solid (100 g), described hereinabove, is heated at 700° C. in flowing air for 2 hours, then cooled to room temperature in air. The cooled acidic mordenite is mixed with 2000 ml of 6N nitric acid and maintained for 2 hours at refluxing temperature under vigorous stirring. After cooling to room temperature the solid is isolated by filtration and washed with water until free of residual acid. The washed solid is dried in air at 110° C. The resulting solid is washed with water until free of residual acid and dried in air at 100° C. to yield the acidic mordenite catalyst of the invention. Analysis of the catalyst by previously described methods gives the following results: a Symmetry Index of 2.23; a Langmuir surface area of 624 m$^2$/g; a total pore volume of 0.52 cc/g; a micropore volume of 0.17 cc/g; a mesopore volume of 0.07 cc/g; a macropore volume of 0.28 cc/g; and a combined ratio of mesopore and macropore volume to total pore volume of 0.67. The catalyst is activated by heating in air at 700° C. for 2 hours.

EXAMPLE 17

Alkylation of Benzene

Benzene (500 g) and the catalyst of Example 16 (10 g) are contacted with propylene at a pressure of 100 psig and a temperature of 120° C. for 16.7 hours. Analysis of the product mixture gives the following results: conversion of benzene, 70.6 percent; yield of cumene, 12.8 percent; meta-diisopropylbenzene, 7.9 percent; and para-diisopropylbenzene, 49.5 percent. The para/meta ratio is 6.3. It is seen that benzene is alkylated predominantly to the para dialkylated isomer.

EXAMPLE 18

Alkylation of t-Butylbenzene t-Butylbenzene (500 g) and the catalyst of Example 16 (10 g) are contacted with propylene at a pressure of 120 psig and a temperature of 150° C. for 20 hours. Analysis of the product mixture gives the following results: conversion of t-butylbenzene 32 percent; yield of para-isopropyl-t-butylbenzene, 20.4 percent; meta-isopropyl-t-butylbenzene, 7.1 percent; and ortho-isopropyl-t-butylbenzene, 0.3 percent. The para/meta ratio is 2.9. It is seen that t-butylbenzene is alkylated predominantly to the para dialkylated isomer.

What is claimed is:

1. A process of alkylating an aromatic compound to a mixture of substituted aromatic compounds enriched in the linear alkylated isomers comprising contacting an aromatic compound with an alkylating agent having from one to eight carbon atoms in the presence of a catalyst under conditions such that a mixture of substituted aromatic compounds enriched in the linear alkylated isomers is formed, said catalyst consisting essentially of an acidic mordenite zeolite having a silica/alumina molar ratio of at least 15:1 and a crystalline structure which is determined by X-ray diffraction to possess a Symmetry Index sufficient to increase the yield of linear alkylated isomers to at least about 20 mole percent.

2. The process of claim 1 wherein the aromatic compound is monocyclic.

3. The process of claim 2 wherein the aromatic compound is represented by the formula:

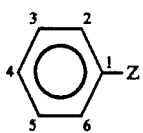

wherein Z is hydrogen, sulfhydryl, alkyl of $C_{1-10}$ carbon atoms, aliphatic alkoxy or thioalkoxy of $C_{1-10}$ carbon atoms, fluoro, chloro, or bromo.

4. The process of claim 3 wherein the aromatic compound is selected from the group consisting of benzene and cumene.

5. The process of claim 2 wherein the Symmetry Index is at least about 1.5.

6. The process of claim 1 wherein the aromatic compound is a $C_{10}-C_{24}$ fused or non-fused polycyclic aromatic compound.

7. The process of claim 6 wherein the non-fused polycyclic aromatic compound is represented by the formula:

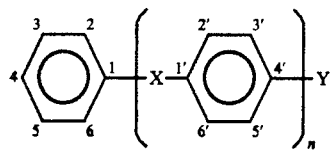

wherein n is a positive number from 1 to 3; Y is hydrogen, hydroxyl, sulfhydryl, alkyl of $C_{1-10}$ carbon atoms, aliphatic alkoxy or thioalkoxy of $C_{1-10}$ carbon atoms, fluoro, chloro, or bromo: and X is absent or is O, S, SO, $SO_2$, $CH_2$, $CH_2CH_2$, $CH_2CH_2CH_2$ or $CHCH_3$.

8. The process of claim 7 wherein the polycyclic aromatic compound is biphenyl, naphthalene, or diphenyl ether.

9. The process of claim 8 wherein the polycyclic aromatic compound is biphenyl.

10. The process of claim 8 wherein the polycyclic aromatic compound is diphenylether.

11. The process of claim 6 wherein the Symmetry Index is at least about 1.0.

12. The process of claim 1 wherein the alkylating agent is a monoolefin, a diolefin, or an alcohol.

13. The process of claim 12 wherein the monoolefin is propylene, n-butene, 1-hexene, cyclohexene, or 1-octene.

14. The process of claim 13 wherein the olefin is propylene.

15. The process of claim 13 wherein the olefin is n-butene.

16. The process of claim 1 wherein the temperature is in the range from about 100° C. to about 400° C.

17. The process of claim 1 wherein the aromatic compound is in the neat, liquid state and the alkylating agent is dissolved in the liquid state.

18. The process of claim 1 wherein the aromatic compound is dissolved in a solvent.

19. The process of claim 18 wherein the solvent is 1,3,5-triisopropylbenzene or decalin.

20. The process of claim 1 wherein the pressure is in the range from about 10 psig to about 500 psig.

21. The process of claim 1 wherein the yield of total dialkylates ranges from about 25 to about 80 mole percent.

22. The process of claim 1 wherein the catalyst has a silica/alumina molar ratio of at least 50:1, a Symmetry Index from about 1.0 to about 2.3, and a porosity such that the total pore volume is in the range from about 0.18 cc/g to about 0.45 cc/g and the ratio of the combined meso- and macropore volume to the total pore volume is in the range from about 0.25 to about 0.75.

23. The process of claim 1 wherein the yield of the linear alkylated isomers is at least about 40 mole percent.

24. The process of claim 23 wherein the yield of the linear alkylated isomers is at least about 70 mole percent.

25. A process of alkylating biphenyl to a mixture of products enriched in 4,4'-(dialkylate)-1,1'-biphenyl comprising contacting biphenyl with an alkylating agent having from one to eight carbon atoms in the presence of a catalyst under conditions such that the 4,4'-dialkylated isomer is formed in a yield of at least about 20 mole percent, said catalyst consisting essentially of an acidic mordenite zeolite having a silica/alumina molar ratio of at least 15:1 and a crystalline structure which is determined by X-ray diffraction to possess a Symmetry Index of at least about 1.0.

26. A process of alkylating benzene to a mixture of products enriched in para-dialkylated benzene comprising contacting benzene with an alkylating agent having from one to eight carbon atoms in the presence of a catalyst under conditions such that the para-dialkylated isomer is formed in a yield of at least about 20 mole percent, said catalyst consisting essentially of an acidic mordenite zeolite having a silica/alumina molar ratio of at least 15:1 and a crystalline structure which is determined by X-ray diffraction to possess a Symmetry Index of at least about 1.5.

27. A process of alkylating a polycyclic aromatic compound to a mixture of substituted polycyclic aromatic compounds enriched in the linear alkylated isomers comprising contacting a polycyclic aromatic compound with an alkylating agent having from one to eight carbon atoms in the presence of a catalyst under conditions such that a mixture of substituted polycyclic aromatic compounds enriched in the linear alkylated isomers is formed, said catalyst consisting essentially of an acidic mordenite zeolite having a silica/alumina molar ratio of at least 15:1 and a crystalline structure which is determined by X-ray diffraction to possess a Symmetry Index of at least 1.0.

28. A process of alkylating a monocyclic aromatic compound to a mixture of substituted monocyclic aromatic compounds enriched in the linear alkylated isomers comprising contacting a monocyclic aromatic compound with an alkylating agent having from one to eight carbon atoms in the presence of a catalyst under conditions such that a mixture of substituted monocyclic aromatic compounds enriched in the linear alkylated isomers is formed, said catalyst consisting essentially of an acidic mordenite zeolite having a silica/alumina molar ratio of at least 15:1 and a crystalline structure which is determined by X-ray diffraction to possess a Symmetry Index of at least 1.5.

* * * * *